United States Patent
Demas et al.

(10) Patent No.: US 9,770,600 B1
(45) Date of Patent: Sep. 26, 2017

(54) PARTICLE CONCENTRATION AND SEPARATION USING MAGNETS

(71) Applicant: Verily Life Sciences LLC, Mountain View, CA (US)

(72) Inventors: Vasiliki Demas, San Jose, CA (US); Vikram Singh Bajaj, Mountain View, CA (US)

(73) Assignee: Verily Life Sciences LLC, Mountain View, CA (US)

(*) Notice: Subject to any disclaimer, the term of this patent is extended or adjusted under 35 U.S.C. 154(b) by 359 days.

(21) Appl. No.: 14/326,983

(22) Filed: Jul. 9, 2014

(51) Int. Cl.
*A61B 5/145* (2006.01)
*A61N 2/00* (2006.01)
*A61N 2/06* (2006.01)
*A61N 2/02* (2006.01)
*A61B 5/00* (2006.01)

(52) U.S. Cl.
CPC .............. *A61N 2/002* (2013.01); *A61B 5/145* (2013.01); *A61B 5/681* (2013.01); *A61N 2/02* (2013.01); *A61N 2/06* (2013.01)

(58) Field of Classification Search
CPC ............ A61B 5/14532; A61B 5/14546; A61B 5/1486; A61B 5/14539; A61B 5/0031
See application file for complete search history.

(56) References Cited

U.S. PATENT DOCUMENTS

| | | | |
|---|---|---|---|
| 5,348,050 A * | 9/1994 | Ashton | B01J 19/087 137/827 |
| 8,368,396 B2 | 2/2013 | Ueda | |
| 8,409,415 B2 | 4/2013 | Liu | |
| 8,529,428 B2 | 9/2013 | Creighton | |
| 8,569,044 B2 | 10/2013 | Hoon | |
| 8,624,592 B2 | 1/2014 | Lee | |
| 2002/0160231 A1 * | 10/2002 | Schneider | G11B 5/70 428/843 |
| 2009/0152176 A1 * | 6/2009 | Kipp | B03C 1/288 209/562 |
| 2009/0325192 A1 * | 12/2009 | Kirakossian | B01L 3/508 435/7.2 |

(Continued)

FOREIGN PATENT DOCUMENTS

| | | | |
|---|---|---|---|
| NL | WO 2014037880 A1 * | 3/2014 | ......... G01R 33/0213 |
| WO | 2013030601 A1 | 3/2013 | |
| WO | 2013173235 A1 | 11/2013 | |

*Primary Examiner* — Eric Winakur
(74) *Attorney, Agent, or Firm* — McDonnell Boehnen Hulbert & Berghoff LLP

(57) ABSTRACT

A variety of wearable magnetic assemblies are provided that are configured to produce magnetic fields having high field magnitudes and/or high field gradients. These wearable magnetic assemblies are configured to exert forces on magnetic particles disposed in a portion of subsurface vasculature (e.g., a portion of the ulnar artery near the wrist) proximate to the magnetic assemblies. These magnetic assemblies include a plurality of dipolar permanent magnets. The forces can act to attract, slow, speed, separate, or otherwise influence the magnetic particles in various applications. In some embodiments, the magnetic particles are configured to bind to an analyte of interest. The collection, separation, and/or concentration of the magnetic particles can enable detection of one or more properties of the analyte, modification of the analyte, and/or extraction of the analyte bound to the magnetic particles.

12 Claims, 9 Drawing Sheets

(56) References Cited

U.S. PATENT DOCUMENTS

| | | | |
|---|---|---|---|
| 2010/0096581 A1* | 4/2010 | Gleich | B03C 1/01 |
| | | | 252/62.51 R |
| 2012/0135494 A1* | 5/2012 | Murthy | B03C 1/0332 |
| | | | 435/173.9 |
| 2012/0289764 A1 | 11/2012 | Murakami | |
| 2013/0144134 A1* | 6/2013 | Lee | G01N 24/08 |
| | | | 600/309 |
| 2013/0316355 A1 | 11/2013 | Dryga et al. | |
| 2014/0014506 A1* | 1/2014 | Dimitrov | G01N 27/745 |
| | | | 204/400 |
| 2014/0021105 A1 | 1/2014 | Lee | |

* cited by examiner

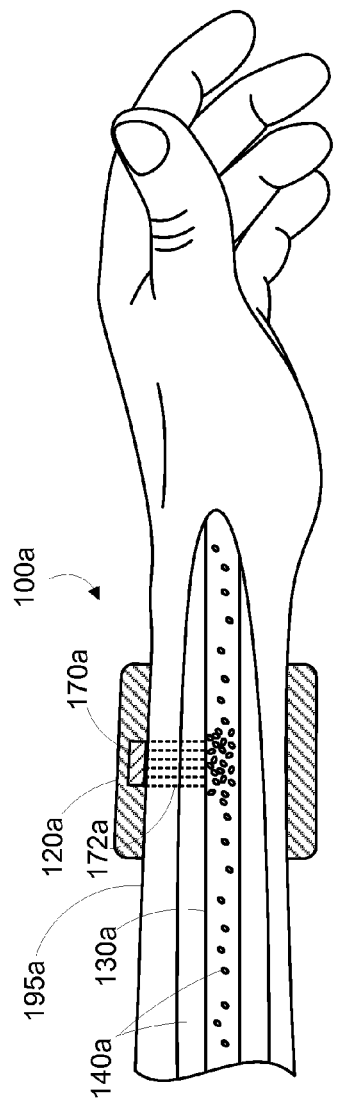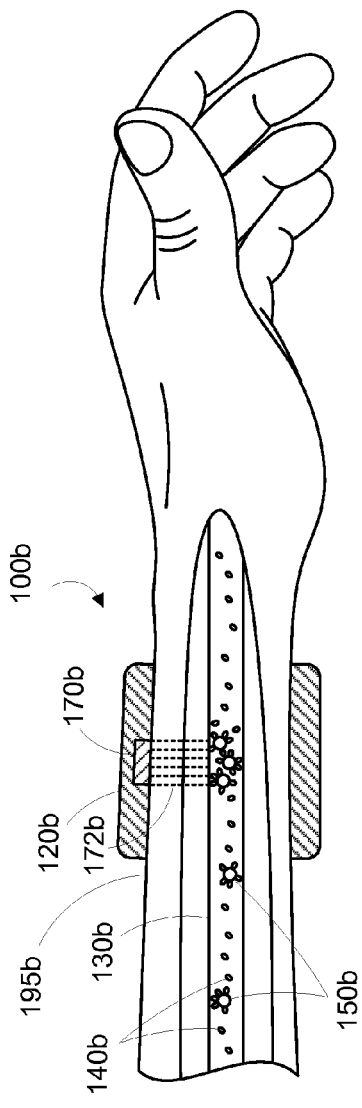

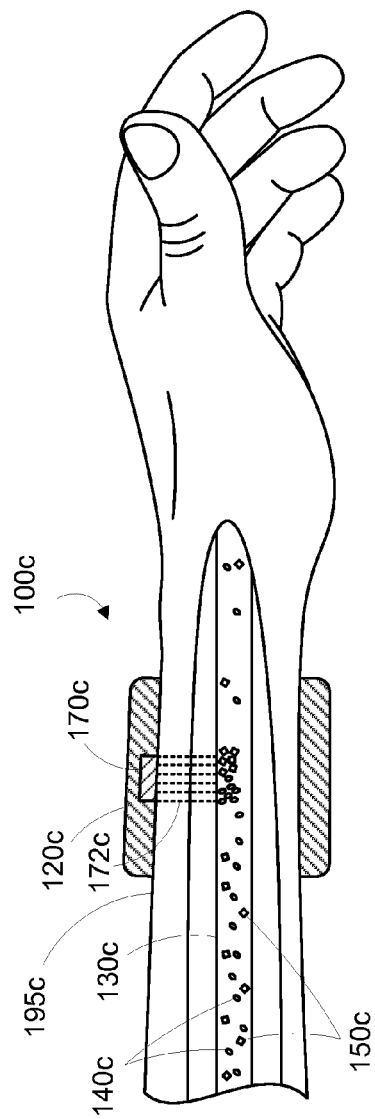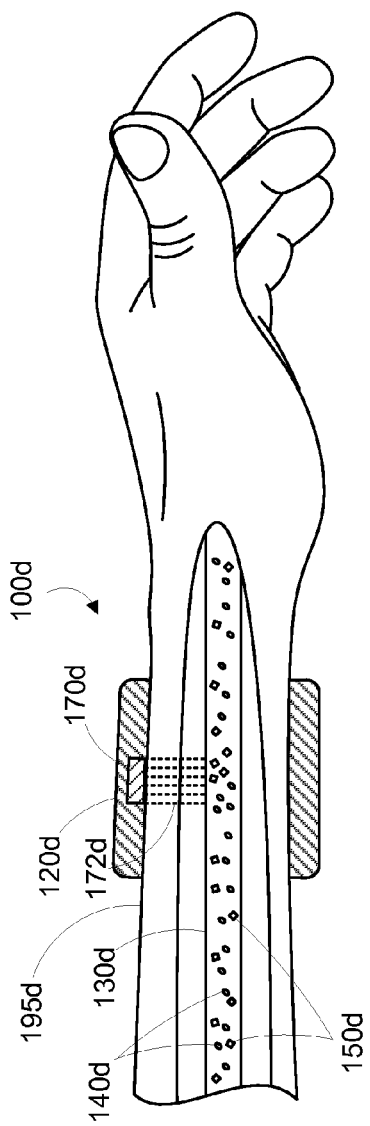

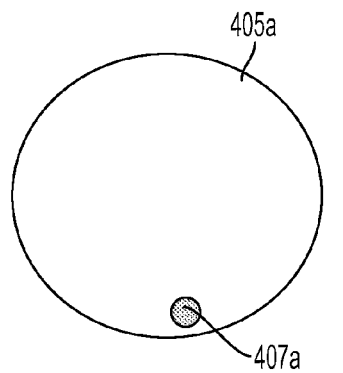
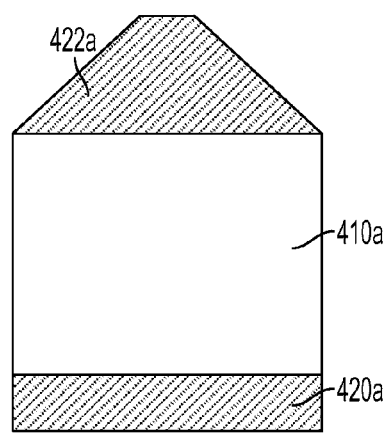
FIG. 4A
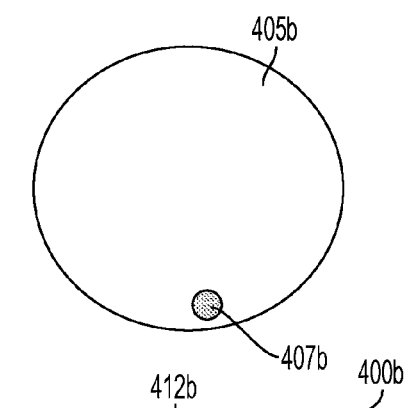
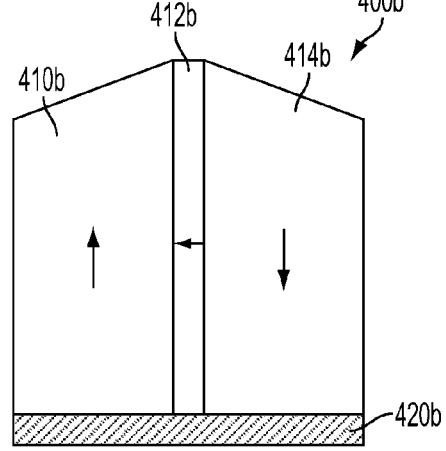
FIG. 4B
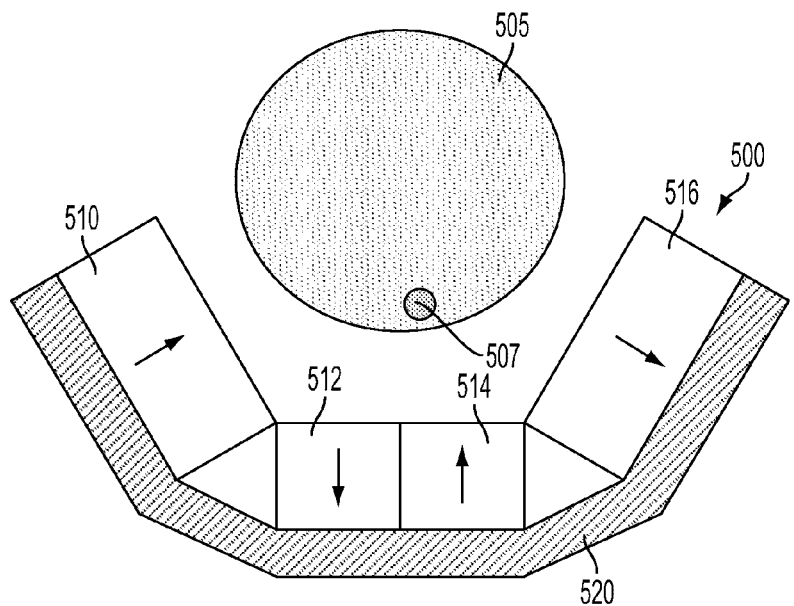
FIG. 5

PARTICLE CONCENTRATION AND SEPARATION USING MAGNETS

BACKGROUND

Unless otherwise indicated herein, the materials described in this section are not prior art to the claims in this application and are not admitted to be prior art by inclusion in this section.

A number of scientific methods have been developed to detect, measure, and/or affect one or more analytes in a biological or other environment. The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities throughout an animal's body is of scientific interest. The one or more analytes could be include pharmaceuticals or other substances introduced into the biological or other environment to effect some chemical or biological process. The one or more analytes could be present in living or nonliving human or animal tissue, and could be detected, measured, of affected in an in vivo, ex vivo, in vitro, or some other type of sample. The one or more analytes could include enzymes, reagents, hormones, proteins, drugs, nanoparticles, pharmaceuticals, cells or other molecules.

Detecting, measuring, and/or affecting one or more analytes in a biological or other environment can be accomplished through the use of a contrast agent targeted to and/or part of the one or more analytes. The contrast agent can facilitate detecting, measuring, and/or affecting the one or more analytes by having an optical, magnetic, electromagnetic, acoustical, and/or some other property that is different from (e.g., that contrasts with) the surrounding environment. The contrast between a property of the surrounding environment and the different property of the contrast agent can permit selective manipulation and/or detection of the contrast agent and/or the one or more analytes.

SUMMARY

Some embodiments of the present disclosure provide a device including a magnetic assembly including a plurality of magnetic elements, wherein the plurality of magnetic elements includes at least a first magnetic element to provide a first magnetic moment and a second magnetic element to provide a second magnetic moment, wherein the first and second magnetic moments have different orientations, wherein the magnetic assembly is configured to be positioned proximate to an external body surface such that (i) the first magnetic moment is oriented toward a portion of subsurface vasculature proximate to the external body surface and the second magnetic moment has a different orientation than the first magnetic moment and (ii) the magnetic assembly is configured for exerting a magnetic force on magnetic particles in the portion of subsurface vasculature.

Some embodiments of the present disclosure present a method, including: (i) positioning a device including a magnetic assembly proximate to an external body surface that is proximate to a portion of subsurface vasculature, wherein the magnetic assembly includes a plurality of magnetic elements, wherein the plurality of magnetic elements includes at least a first magnetic element to provide a first magnetic moment oriented toward the portion of subsurface vasculature and a second magnetic element to provide a second magnetic moment with a different orientation than the first magnetic moment; and (ii) exerting, by the magnetic assembly in the positioned device, a magnetic force on magnetic particles disposed in the portion of subsurface vasculature.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1A is side partial cross-sectional view of an example wrist-mounted device, while on a human wrist.

FIG. 1B is side partial cross-sectional view of an example wrist-mounted device, while on a human wrist.

FIG. 1C is side partial cross-sectional view of an example wrist-mounted device, while on a human wrist.

FIG. 1D is side partial cross-sectional view of an example wrist-mounted device, while on a human wrist.

FIG. 4A is cross-sectional view of an example magnetic assembly, while positioned near a lumen of subsurface vasculature.

FIG. 4B is cross-sectional view of an example magnetic assembly, while positioned near a lumen of subsurface vasculature.

FIG. 5 is cross-sectional view of an example magnetic assembly, while positioned near a lumen of subsurface vasculature.

DETAILED DESCRIPTION

Figure 2A:
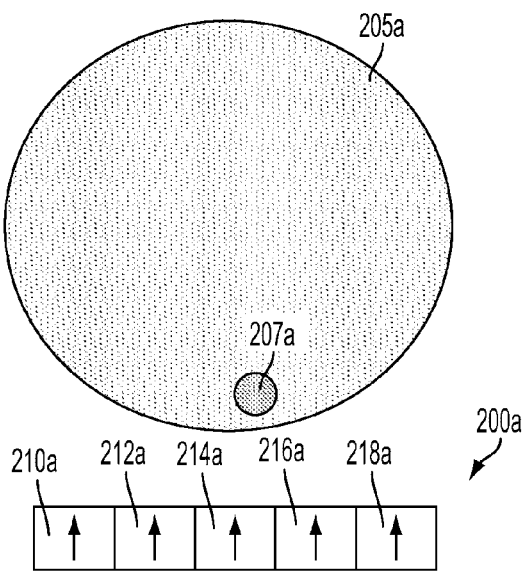
FIG. 2A is cross-sectional view of an example magnetic assembly, while positioned near a lumen of subsurface vasculature.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Magnetic particles can be configured to selectively bind with an analyte of interest. Magnetic particles configured in this way can enable manipulation of, detection of, or other interactions with the analytes by applying magnetic forces to the magnetic particles. Additionally or alternatively, an analyte of interest could be intrinsically magnetic, or could be an engineered analyte (e.g., a pharmaceutical) that has a magnetic property and/or that is bound to a magnetic particle and that can be introduced into an environment according to an application.

Manipulation of, detection of, or other interactions with magnetic particles as described herein can involve magnetic fields having specified properties. In some examples, it can be desirable to direct a magnetic field of a specified large magnitude into a biological environment (e.g., within vasculature of a person's wrist). Additionally or alternatively, it can be desirable to provide a magnetic field having a specified large magnitude of magnetic field gradient. For example, a magnetic field gradient could be used for collection of, partitioning of, or application of force to magnetic particles in a viscous and/or flowing fluid (e.g., blood in a portion of subsurface vasculature of a person). Further, in some applications it can be desirable to generate these magnetic fields using relatively small, low-power devices.

Embodiments herein relate to magnetic assemblies that include magnetic elements (i.e., permanent magnets, electromagnets, and other components that have and/or can be operated to have a magnetic dipole moment) and that are configured to generate high-strength magnetic fields (i.e., magnetic fields having a high field magnitude and/or field gradient magnitude). These embodiments could be applied to manipulate magnetic particles in living (e.g., blood of a living human or animal) or nonliving (e.g., a sample in a container configured to enable imaging or measurement of the sample) biological environments or non-biological environments (e.g., a fluid that is part of a chemical synthesis process). In some embodiments, the magnetic assemblies could be part of a wearable device (e.g., a device configured to be worn around the wrist).

A magnetic assembly could include one or more magnetic elements. The one or more magnetic elements could be configured to produce high-strength magnetic fields. The one or more magnetic elements could be permanent magnets. Example permanent magnets include, without limitation, samarium-cobalt magnets, neodymium magnets, rare earth magnets, alnico magnets, ferrites, or other ferromagnetic or otherwise permanently magnetic materials. The one or more magnetic elements could have a variety of orientations (e.g., directions of the magnetic moment of the one or more magnetic elements) relative to a target environment and relative to each other. In some examples, the one or more magnetic elements are oriented toward the target environment. In some examples, the one or more magnetic elements include two magnetic elements having opposite magnetic orientations. In some examples, the one or more magnetic elements include three or more magnetic elements arranged as a Halbach array (i.e., a substantially locally linear or planar array wherein adjacent magnetic elements have magnetic orientations rotated by 90 degrees relative to each other, and wherein at least one of the magnetic elements of the array has a magnetic orientation perpendicular to the plane or line of the planar or linear array, respectively) in order to increase the magnitude of the magnetic field and/or magnetic field gradient on one side of the three or more magnetic elements and reduce the magnitude of the magnetic field and/or magnetic field gradient on the opposite side of the three or more magnetic elements.

In some embodiments, a magnetic assembly could include one or more magnetic shims or poles, i.e., elements configured to provide a high-permeability region to modify the direction, strength, or other properties of the magnetic field generated by the magnetic assembly. The magnetic shims could have a variety of geometries according to a variety of applications, and could be composed of one or more of a variety of materials having a specified level of permeability. For example, the magnetic shims could include mu-metal, iron, steel, metglas, Permalloy, ferrite, or other materials. In some embodiments, one of the one or more magnetic shims could be disposed on a side of the magnetic assembly opposite the target environment and configured to reduce the amount of magnetic flux produced by the magnetic assembly in a direction opposite the target environment and/or to increase the amount of magnetic flux produced by the magnetic assembly in the target environment. In some embodiments, one of the one or more magnetic shims could be a focusing pole configured to focus flux produced from one or more faces and/or magnetic elements of the magnetic assembly toward the target environment. For example, the focusing pole could have a trapezoidal prism, triangular prism, conical, truncated conical, pyramidal, truncated pyramidal, or other narrowing geometry such that the focusing pole had a first cross-sectional area in contact with elements of the magnetic assembly and a second, smaller cross-sectional area proximate to the target environment.

In some examples, the magnetic assembly could wholly or partially enclose the target environment. For example, the target environment could be a portion of vasculature in a wrist of a human, and the magnetic assembly could be configured to partially wrap around the wrist of the human. The magnetic assembly could include one or a plurality of magnetic elements and/or magnetic shim elements arranged around the target environment according to a variety of configurations.

Magnetic assemblies as described herein (and devices including such magnetic assemblies) could be configured to provide a number of different applications related to magnetic particles (or other magnetic materials) in a target environment. In some examples, these applications are enabled by the magnetic particles being configured to bind to one or more analytes of interest. For example, the one or more analytes could be any analytes that, when present in or absent from the blood of a human, or present at a particular concentration or range of concentrations, may be indicative of a medical condition or health of the human. The one or more analytes could include enzymes, hormones, proteins, cells or other substances. In some examples, the applications are enabled by the magnetic particles, or chemicals, enzymes, or other moieties attached and/or bound to the magnetic particles, being configured to cause some chemical or biological effect in the target environment. For example, the magnetic particles could be attached to a pharmaceutical.

Applications of magnetic assemblies configured to exert forces on magnetic particles configured to selectively interact with one or more analytes could include detecting, measuring, and/or altering one or more properties of the one or more analytes. For example, the magnetic assembly could be configured to exert an attractive magnetic force on the magnetic particles such that the magnetic particles collected in the target environment (e.g., a portion of subsurface vasculature) proximate to a detector or other component configured to detect, measure, and/or alter one or more properties of the one or more analytes. In some examples, the one or more analytes could have a low concentration, such that a signal-to-noise ratio of a measurement of the one or more properties of the one or more analytes is increased due to the collection of the magnetic particles proximate to the detector. In some examples, an energy emitter could be configured to emit an energy sufficient to destroy, denature, or otherwise alter one or more properties of the one or more analytes. Collection proximate to the energy emitter of the one or more analytes bound to the magnetic particles can enable the energy emitter to effect a specified level or degree of alteration of the one or more analytes. Additionally or alternatively, the magnetic assembly could be configured to partition the magnetic particles based on whether individual magnetic particles are bound to the one or more analytes, and the detection, measurement, and/or alteration of the analyte could be related to the partitioning of the magnetic particles based on binding to the one or more analytes. Other applications and configurations are anticipated.

The magnetic assembly could be configured to affect a rate of reaction, rate of activity, or other rate of modification of the one or more analytes. In some examples, an analyte (e.g., a pharmaceutical) could be removed from the target environment (e.g., by ultrafiltration through kidneys operatively coupled to a portion of subsurface vasculature) at a first rate in the absence of the magnetic particles and/or magnetic assembly. The introduction to the target environment of the magnetic particles configured to selectively bind to the one or more analytes, and the presence of the magnetic assembly configured to attract the magnetic particles proximate to the target environment, could result in the analyte being removed from the target at a second rate that is lower than the first rate. Further, one or more properties of the magnetic assembly (e.g., the proximity of the magnetic assembly to the target environment) could be controlled to control the rate at which the analyte is removed from the target environment.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Illustrative Magnetic Particles

In some examples, magnetic assemblies (and devices incorporating such magnetic assemblies) as described herein exert magnetic forces on magnetic particles disposed in a fluid environment. The fluid environment could include artificial environments (e.g., a fluid of an industrial process, a fluid of a chemical or pharmaceutical process) and natural environments (e.g., a lake, a river, a march, blood in vasculature of an animal). For example, the magnetic particles could be disposed in blood in a portion of subsurface vasculature of a human. The magnetic particles could be permanently magnetized (e.g., could be ferromagnetic) or could become magnetized when exposed to a magnetic field (e.g., could be paramagnetic) or to some other factor. A magnetic assembly exerting a magnetic force on such magnetic particles could include providing a magnetic field in the environment of the magnetic particles having a high magnitude of magnetic field gradient, such that permanent and/or induced magnetic moments of the magnetic particles are attracted in the direction of the gradient. A magnetic assembly exerting a magnetic force on such magnetic particles could additionally or alternatively include providing a magnetic field in the environment of the magnetic particles having a high magnitude, such that magnetic moments are induced in the magnetic particles and/or permanent and/or induced magnetic moments of the magnetic particles experience a torque aligning the magnetic moments with the direction of the magnetic field.

Generally, the magnitude of a magnetic force exerted on a magnetic particle is related to the magnitude of the permanent and/or induced magnetic dipole moment of the magnetic particle. In some examples, the magnitude of the permanent and/or induced magnetic dipole moment can be related to the mass and/or volume of magnetic material included in the magnetic particle. For example, the magnitude of the induced magnetic dipole moment of a magnetic particle that includes a particle of superparamagnetic iron oxide could be related to the volume of the particle of superparamagnetic iron oxide. The magnetic particles could be artificial (e.g., functionalized polystyrene shells containing and/or coating particles of superparamagnetic iron oxide), natural (e.g., particles of magnetite encapsulated in lipid bilayers in a cell), or could contain natural and artificial elements (e.g., an artificial magnetic particle onto which a variety of natural antibodies are adsorbed or otherwise attached).

Generally, the magnetic particles may be made of and/or wholly or partially coated by an inert material, such as polystyrene, and can have a diameter that is less than about 20 micrometers. In some embodiments, the magnetic particles have a diameter on the order of about 10 nm to 1 μm. In further embodiments, small particles on the order of 10-100 nm in diameter may be assembled to form a larger "clusters" or "assemblies" on the order of 1-10 micrometers. Those of skill in the art will understand a "particle" in its broadest sense and that it may take the form of any fabricated material, a molecule, tryptophan, a virus, a phage, etc. Further, a magnetic particle may be of any shape, for example, spheres, rods, non-symmetrical shapes, etc. In some examples, a magnetic material of the magnetic particles can include a paramagnetic, super-paramagnetic or ferromagnetic material or any other material that responds to a magnetic field. In some examples, the magnetic particles can include a magnetic moiety. Further, the particles can be configured to selectively bind to one or more analytes (e.g., chemicals, hormones, peptides, DNA or RNA fragments, cells). In some examples, the magnetic particles could be considered to include other elements (e.g., analytes, other magnetic or non-magnetic particles) bound to the magnetic particles. For example, a 'first magnetic particle' could include a particle of magnetic material functionalized to selectively interact with an analyte, and a 'second magnetic particle' could include one or more of the 'first magnetic particles' bound to the analyte, such that the 'second magnetic particle' is a composite particle including at least one instance of the analyte. Other embodiments of magnetic particles are anticipated.

In some examples, the magnetic particles are functionalized to selectively interact with an analyte of interest. The magnetic particles can be functionalized by covalently attaching a bioreceptor designed to selectively bind or otherwise recognize a particular analyte (e.g., a clinically-relevant analyte, e.g., a cancer cell). For example, magnetic particles may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), or plasmids. The functionalized magnetic particles can be introduced into a portion of subsurface vasculature of a person by injection, ingestion, inhalation, transdermal application, or in some other manner.

A clinically-relevant analyte could be any substance that, when present in the blood of a person or animal, or present at a particular concentration or range of concentrations, may directly or indirectly cause an adverse medical condition. For example, the clinically-relevant analyte could be an enzyme, hormone, protein, other molecule, or even whole or partial cells. In one relevant example, certain proteins have been implicated as a partial cause of Parkinson's disease. Thus, the development of Parkinson's disease might be prevented or retarded by providing magnetic particles functionalized with a bioreceptor that will selectively bind to this target. A magnetic force may then be exerted on these bound magnetic particles, using one or more magnetic assemblies as described herein (e.g., a magnetic assembly in a device positioned proximate to an external body surface that is proximate to a portion of subsurface vasculature), to collect, separate, detect, modify, or otherwise interact with the bound protein. As a further example, the analyte could be a cancer cell. By selectively collecting and then detecting, extracting (e.g., by use of an intravenous syringe), modifying, or destroying individual cancer cells (e.g., by emitting energy toward the magnetic particles such that the magnetic particles are heated sufficiently to cause an increase in temperature of the proximate bound cancer cells), the spread of cancer may be diminished and/or quantified.

Magnetic particles and/or magnetic assemblies configured to exert magnetic forces on such magnetic particles (and devices including such magnetic assemblies) could be configured and/or operated to provide a number of different applications. Applications could include detecting one or more properties of the magnetic particles, one or more properties of an analyte bound to or otherwise selectively interacting with the magnetic particles, collecting and/or extracting the magnetic particles and/or analytes bound to the magnetic particles, modifying and/or destroying the magnetic particles and/or analytes bound to the magnetic particles, or other applications.

A magnetic assembly exerting a force on magnetic particles could include exerting an attractive magnetic force on the magnetic particles. That is, the magnetic assembly could be configured to attract the magnetic particles toward the magnetic assembly. In some examples, the magnetic assembly could be configured to exert an attractive magnetic force of sufficient magnitude to collect the magnetic particles proximate to the magnetic assembly. For example, the magnetic particles could be disposed in blood of a wearer of a wearable device that includes the magnetic assembly, and the wearable device including the magnetic assembly could be mounted to an external body surface of the wearer proximate to the portion of subsurface vasculature such that the magnetic particles collect in the portion of subsurface vasculature proximate to the magnetic assembly. Additionally or alternatively, the magnetic assembly could be disposed in a desktop device, in a device mounted and/or installed in a floor, wall, or ceiling of a room, or in some other device and the device and/or a portion of the body of the wearer could be positioned such that the magnetic particles collect in the portion of subsurface vasculature proximate to the magnetic assembly.

FIG. 1A is a partial cross-sectional side view of a human wrist illustrating the operation of an example wrist-mounted device. In the example shown in FIG. 1A, the wrist-mounted device 100*a* includes a magnetic assembly 170*a* mounted on a strap or wrist-band 120*a* and oriented on the anterior side 195*a* of the wearer's wrist. Magnetic particles 140*a* have been introduced into a lumen of subsurface vasculature 130*a* of the human by one of the means discussed herein. Magnetic assembly 170*a* generates a magnetic field 172*a* that exerts a magnetic force sufficient to cause magnetic particles 140*a* present in a lumen of the subsurface vasculature 130*a* to collect in a region proximal to the magnetic assembly 170*a*.

The forces exerted by magnetic assemblies as described herein could be attractive (i.e., toward the magnetic assembly) or could be directed in other directions. For example, the magnetic forces exerted by the magnetic assembly could be directed away from the magnetic assembly, in a direction parallel to a flow of fluid in which the magnetic particles are disposed (e.g., in the direction of or against the direction of blood flowing in a portion of subsurface vasculature), or in some other direction according to an application. Generally, the magnitude of the magnetic force exerted on a magnetic particle can be related to the volume of the magnetic particle (i.e., to an amount of magnetic material in the particle) while the magnitude of fluid forces (e.g., drag, convective forces) on a magnetic particle can be related to a surface area and/or effective cross-sectional area of the magnetic particle.

As such, first magnetic particles can experience a first magnetic force (and/or ratio of magnetic to fluid force) such that the first magnetic particles are separated from, differentially collected relative to, or otherwise differently affected by the magnetic assembly relative to second magnetic particles. The second magnetic particles have different properties (e.g., size, degree of aggregation, binding state) relative to the first magnetic particles and experience a second magnetic force (and/or ratio of magnetic to fluid force) that is different from the first magnetic force and/or ratio of magnetic to fluid force. Separation, differential collection, or other differential effects of two or more groups of magnetic particles could be dependent on one or more properties of an environment containing the two or more groups of magnetic particles, e.g., a flow rate and/or flow profile or fluid in the containing environment. For example, separation and collection of two or more groups of magnetic particles in a portion of subsurface vasculature could be related to a flow rate of blood in the portion of subsurface vasculature.

FIG. 1B is a partial cross-sectional side view of a human wrist illustrating the operation of an example wrist-mounted device. In the example shown in FIG. 1B, the wrist-mounted device 100*b* includes a magnetic assembly 170*b* mounted on a strap or wrist-band 120*b* and oriented on the anterior side 195*b* of the wearer's wrist. Magnetic particles 140*b* have been introduced into a lumen of subsurface vasculature 130*b* of the human by one of the means discussed herein. Magnetic particles 140*b* are configured to bind to an analyte 150*b* that is also present within the lumen of subsurface vasculature 130*b*. One or more magnetic particles 140*b* bound to an instance of the analyte 150b form an aggregate particle having properties different from individual unbound magnetic particles 140b. Magnetic assembly 170b generates a magnetic field 172b that exerts a magnetic force sufficient to cause aggregate particles (i.e., one or more magnetic particles 140b bound to an instance of the analyte 150b) present in a lumen of the subsurface vasculature 130b to collect in a region proximal to the magnetic assembly 170b while substantially allowing unbound magnetic particles 140b to flow past the lumen of subsurface vasculature 130b proximate to the magnetic assembly 170b.

In some examples, magnetic forces could be exerted on more than one type of magnetic particles in an environment. The magnetic forces could be different according to the type of magnetic particles and could be related to corresponding different properties of the types of magnetic particles. The different type of magnetic particles could be collected at respective different locations in an environment (e.g., a lumen of subsurface vasculature) and/or could be collected or otherwise differentially manipulated by a magnetic assembly to enable a variety of applications.

FIG. 1C is a partial cross-sectional side view of a human wrist illustrating the operation of an example wrist-mounted device. In the example shown in FIG. 1C, the wrist-mounted device 100c includes a magnetic assembly 170c mounted on a strap or wrist-band 120c and oriented on the anterior side 195c of the wearer's wrist. First magnetic particles 140c and second magnetic particles 150c have been introduced into a lumen of subsurface vasculature 130c of the human by one of the means discussed herein. Magnetic assembly 170c generates a magnetic field 172c that exerts a magnetic force sufficient to first 140c and second 150c magnetic particles present in the lumen of the subsurface vasculature 130c to collect in respective regions proximal to the magnetic assembly 170c. This collection in separate regions could be related to the magnetic assembly 170c exerting a greater attractive force on the first magnetic particles 140c, the first magnetic particles 140c being subject to less drag or other fluid forces, the magnetic assembly 170c exerting forces on the first 140c and second 150c magnetic particles parallel to the direction of flow in the lumen of subsurface vasculature 130c, or could be related to additional or alternative factors. In some examples, more than two types of magnetic particles could be attracted to respective more than two locations relative to the magnetic assembly 170c. In some examples, magnetic particles could have a range of properties related to a range of collection locations relative to the magnetic assembly 170c (e.g., the magnetic particles could be arranged topographically relative to a property of the magnetic particles, e.g., the magnetic particles could be arranged from largest to smallest, or according to some other property or combination of properties).

In some examples, a magnetic assembly could exert magnetic forces on magnetic particles in an environment without collecting the magnetic particles. FIG. 1D is a partial cross-sectional side view of a human wrist illustrating the operation of an example wrist-mounted device. In the example shown in FIG. 1D, the wrist-mounted device 100d includes a magnetic assembly 170d mounted on a strap or wrist-band 120d and oriented on the anterior side 195d of the wearer's wrist. First magnetic particles 140d and second magnetic particles 150d have been introduced into a lumen of subsurface vasculature 130d of the human by one of the means discussed herein. Magnetic assembly 170d generates a magnetic field 172d that exerts a magnetic force sufficient to first 140d and second 150d magnetic particles present in the lumen of the subsurface vasculature 130d to separate in the region proximal to the magnetic assembly 170d. This separation could be related to the first magnetic particles 140d being subject to less drag or other fluid forces, the magnetic assembly 170d exerting forces on the first 140d and second 150d magnetic particles parallel to the direction of flow in the lumen of subsurface vasculature 130d, or could be related to additional or alternative factors. In some examples, more than two types of magnetic particles could be separated in a direction/region relative to the magnetic assembly 170d. In some examples, magnetic particles could have a range of properties related to a range separation magnitudes/regions relative to the magnetic assembly 170d (e.g., the magnetic particles could be slowed/sped in a flow to a degree relative to a property of the magnetic particles, e.g., the largest magnetic particles could be slowed the most while the smallest magnetic particles could be slowed the least, or according to some other property or combination of properties).

Other manipulations and/or magnetic forces could be applied to magnetic particles in an environment than those described above. The manipulations and/or magnetic forces could be related to properties of the magnetic particles (e.g., size, magnetic dipole moment, drag coefficient, cross-sectional area, degree of aggregation with other magnetic particles, whether the magnetic particles is bound to an analyte), properties of the environment containing the magnetic particles (e.g., a viscosity, a pH, a degree of polarity of a solvent, a flow rate, a flow profile, a degree of turbulence), or other factors. For example, magnetic particles could be collected or otherwise manipulated in a manner related to where in a flow the articles are located, e.g., magnetic particles in low-flow-rate regions could be collected while magnetic particles in high-flow regions could not be collected.

Magnetic assemblies, devices containing magnetic assemblies, magnetic particles, and other aspects and embodiments described herein could be configured and/or operated to provide a variety of applications. In some examples, magnetic particles could be configured to bind to an analyte of interest, and a magnetic assembly could be configured to collect or otherwise manipulate the magnetic particles to enable the detection, extraction, modification, or other manipulation of the analyte. For example, a detector could be disposed proximate to a magnetic assembly that is configured to collect the magnetic particles, and the detector could detect one or more properties of the analyte bound to the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the collected magnetic particles sufficient to alter one or more properties of the analyte (e.g., to destroy, denature, heat, change a conformation state of, other otherwise modify the analyte). In some examples, collection of an analyte bound to magnetic particles by a magnetic assembly could enable the extraction of the analyte and magnetic particles (e.g., using a hypodermic needle).

In some applications, manipulation of magnetic particles could enable detection and/or modification of an analyte. For example, the reaction (e.g., a differential and/or absolute motion) of a magnetic particle to a magnetic field generated by a magnetic assembly could be detected, and one or more properties of the reaction could be used to determine one or more properties of the magnetic particle. For example, a change in velocity of a magnetic particle, when exposed to the magnetic field of the magnetic assembly, could be related to whether the magnetic particle was bound to an analyte. In some examples, the magnetic particles could be configured to couple an oscillating electromagnetic field into an increase in heat proximate to the magnetic particle, and this increase in heat could be used to detect one or more properties of the magnetic particle and/or to modify the environment proximate to the particle (e.g., to denature an analyte bound to the magnetic particle). Other configurations, operations, and applications of the embodiments described herein are anticipated.

The terms "binding", "bound", and related terms used herein are to be understood in their broadest sense to include any interaction between the receptor and the target or another functionalized particle such that the interaction allows the target to be modified or destroyed by energy emitted from a device.

III. Example Devices

In some applications, it can be desirable to produce magnetic fields having high magnitude, high magnitude of field gradient, a specified field profile, or other properties using a small device and using minimal power. For example, an application could include a wearable device configured to be powered by a battery disposed in the device and to attract magnetic particles in the body of a wearer of a device. Such magnetic fields could be produced by magnetic assemblies that include magnetic elements (i.e., permanent magnets, electromagnets, and other components that have and/or can be operated to have a magnetic dipole moment), paramagnetic materials, flux-focusing and/or shielding shims or poles, or other elements. A class of such magnetic elements includes unpowered elements, e.g., permanent magnets and other magnetic materials capable of generating a magnetic field having a desired profile, magnitude, or other property while requiring significantly no applied power.

Such magnetic assemblies could include one or more magnetic elements, with each magnetic element of the one or more magnetic elements having a respective magnetic moment that is oriented relative to an environment of interest (e.g., a portion of subsurface vasculature of a user of a device that includes the one or more magnetic elements) to enable some application (e.g., the exertion of a magnetic force to enable collection, separation, or some other manipulation of one or more magnetic particles in the portion of subsurface vasculature). The magnetic assembly could include two or more magnetic elements arranged to provide a specified magnetic field in the environment proximate to the magnetic elements. For example, the magnetic assembly could include a first magnetic element that provides a magnetic moment oriented toward a portion of subsurface vasculature, and a second magnetic element that provides a magnetic moment oriented away from the portion of subsurface vasculature, such that a region between the opposite poles of the first and second magnetic elements had a desired high magnitude of magnetic field gradient or some other specified property. Magnetic assemblies could additionally or alternatively include magnetic shims or poles (e.g., materials having high magnetic permeability or some other specified magnetic property) configured to focus magnetic flux toward a specified region of an environment and/or shield a specified region of an environment from magnetic flux.

FIG. 2A illustrates a schematic diagram of an example magnetic assembly 200a comprising a plurality of magnetic elements 210a, 212a, 214a, 216a, 218a having respective magnetic moments (arrows). The magnetic assembly 200a is positioned proximate to a portion of subsurface vasculature 207a within a body of a human 205a. The magnetic assembly 200a could be part of a wearable device and the wearable device could further include a mount configured to mount the wearable device to an external body surface of the body of the human 205a proximate to the portion of subsurface vasculature 207a. The permanent magnets 210a, 212a, 214a, 216a, 218a of the magnetic assembly 200a can be configured to exert a magnetic force on magnetic particles in the portion of subsurface vasculature 207a.

Magnetic elements of a magnetic assembly could have magnetic moments oriented in substantially the same direction (as illustrated in the example of FIG. 2A) or could have a number of orientations relative to each other and/or to an environment of interest. In some examples, the orientations of the magnetic moments could be specified to increase one or more properties of a generated magnetic field (e.g., a field magnitude, a magnitude of a field gradient) in a first region and/or to reduce one or more properties of the generated magnetic field in a second region. For example, the magnetic moments of three or more magnetic elements in a magnetic assembly could be arranged as a Halbach array to increase the magnitude of the magnetic field on one side of the magnetic assembly and to decrease the magnitude of the magnetic field on an opposite side of the magnetic assembly.

Figure 2B:
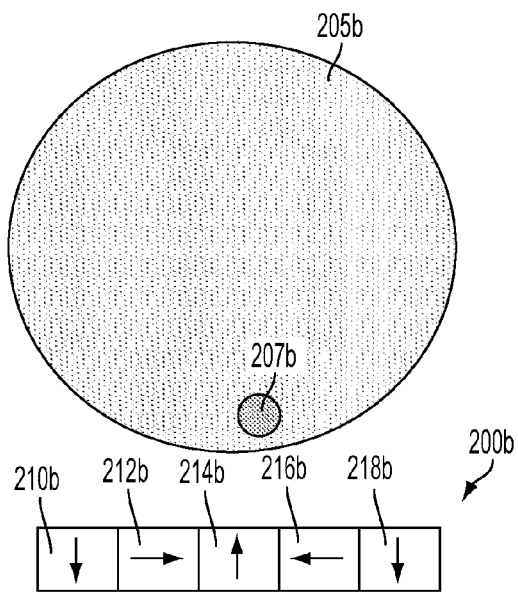
FIG. 2B is cross-sectional view of an example magnetic assembly, while positioned near a lumen of subsurface vasculature.

FIG. 2B illustrates a schematic diagram of an example magnetic assembly 200b comprising a plurality of magnetic elements 210b, 212b, 214b, 216b, 218b having respective magnetic moments (arrows) oriented such that the magnetic assembly forms a Halbach array. The magnetic assembly 200b is positioned proximate to a portion of subsurface vasculature 207b within a body of a human 205b. The magnetic assembly 200b could be part of a wearable device and the wearable device could further include a mount configured to mount the wearable device to an external body surface of the body of the human 205b proximate to the portion of subsurface vasculature 207b. The magnetic elements 210b, 212b, 214b, 216b, 218b of the magnetic assembly 200b can be configured to exert a magnetic force on magnetic particles in the portion of subsurface vasculature 207b. The magnetic elements 210b, 212b, 214b, 216b, 218b being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic assembly and/or an environment of interest proximate to the magnetic assembly are anticipated.

In some examples, the magnetic assembly could wholly or partially enclose an environment (e.g., an aspect of a body of a wearer, e.g., a wrist). That is, a magnetic assembly and/or a wearable or other device including a magnetic assembly could have a concave surface configured to at least partially enclose a corresponding convex surface of an environment of interest (e.g., the magnetic assembly could have a concave surface configured to at least partially enclose a convex shape of an external body surface of a human or other user of the magnetic assembly). Further, one or more of a plurality of magnetic elements of the magnetic assembly could be disposed on the concave surface of the magnetic assembly.

Figure 2C:
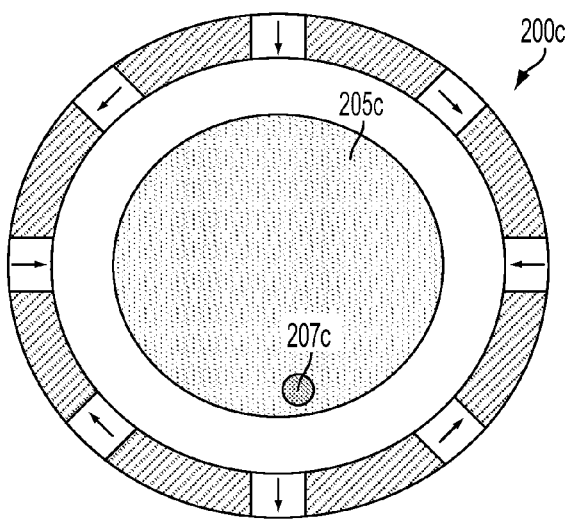
FIG. 2C is cross-sectional view of an example magnetic assembly, while positioned near a lumen of subsurface vasculature.
Figure 2D:
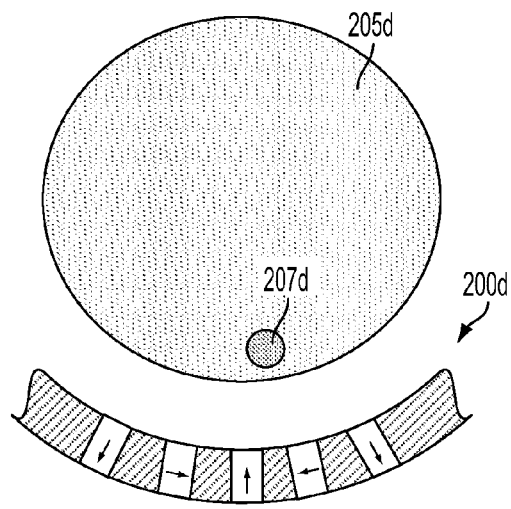
FIG. 2D is cross-sectional view of an example magnetic assembly, while positioned near a lumen of subsurface vasculature.

FIGS. 2C and 2D illustrate schematic diagrams of example magnetic assemblies 200c, 200d comprising respective pluralities of magnetic elements (arrows) oriented such that the magnetic assemblies 200c, 200d form respective configurations of Halbach arrays. The magnetic assemblies 200c, 200d are positioned proximate to respective portions of subsurface vasculature 207c, 207d within respective bodies of respective humans 205c, 205d. The magnetic assemblies 200c could be part of respective wearable devices and the wearable devices could further include mounts configured to mount the wearable devices to respective external body surfaces of the bodies of the respective humans 205c, 205d proximate to the respective portions of subsurface vasculature 207c, 207d. The magnetic elements of the magnetic assemblies 200c, 200d can be configured to exert magnetic forces on magnetic particles in respective portions of subsurface vasculature 207c, 207d.

Magnetic assemblies can include magnetic poles (also called magnetic shims) configured to focus, block, or otherwise modify a pattern of magnetic flux and/or a magnetic field profile generated by one or more magnetic elements. The magnetic poles can have a variety of specified geometries and be composed of a variety of materials according to a variety of applications. The magnetic poles could be composed of materials having a specified magnetic property (e.g., permeability, reluctance, susceptibility, coercivity, remanence, saturation level). For example, the magnetic poles could be composed of one or more materials having a high magnetic permeability, e.g., mu-metal, iron, steel, metglas, Permalloy, ferrite, or other materials.

Figure 3A:
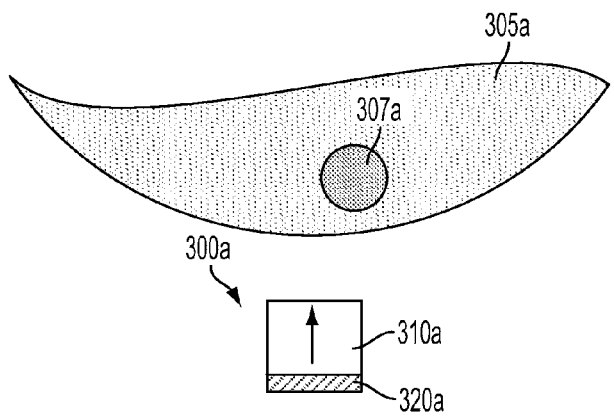
FIG. 3A is cross-sectional view of an example magnetic assembly, while positioned near a lumen of subsurface vasculature.

FIG. 3A illustrates a schematic diagram of an example magnetic assembly 300a comprising a magnetic element 310a having a magnetic moment (arrow) and a magnetic pole 320a comprising a high-permeability material. The magnetic assembly 300a is positioned proximate to a portion of subsurface vasculature 307a within a body of a human 305a. The magnetic pole 320a comprises a layer of the high-permeability material disposed on a side of the magnetic assembly 300a opposite the human body 305a. The magnetic assembly 300a could be part of a wearable device and the wearable device could further include a mount configured to mount the wearable device to an external body surface of the body of the human 305a proximate to the portion of subsurface vasculature 307a. The magnetic element 310a and pole 320a of the magnetic assembly 300a can be configured to exert a magnetic force on magnetic particles in the portion of subsurface vasculature 307a. Further, the magnetic pole 320a could act to increase a property (e.g., a magnitude, a gradient magnitude) of the magnetic field produced by the magnetic assembly 300a in the portion of subsurface vasculature 307a and to decrease a property (e.g., a magnitude, a gradient magnitude) of the magnetic field produced by the magnetic assembly 300a in a region away from the body of the human 305a (i.e., to 'shield' the region below the magnetic assembly 300a from the magnetic field produced by the magnetic element 310a).

Figure 3B:
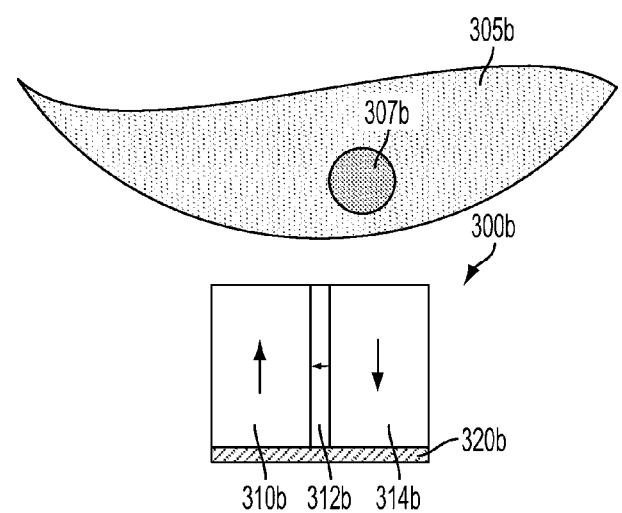
FIG. 3B is cross-sectional view of an example magnetic assembly, while positioned near a lumen of subsurface vasculature.

FIG. 3B illustrates a schematic diagram of an example magnetic assembly 300b comprising a plurality of magnetic elements 310b, 312b, 314b having respective magnetic moments (arrows) oriented such that the magnetic assembly forms a Halbach array. The magnetic assembly 300b additionally includes a magnetic pole 320a comprising a high-permeability material. The magnetic assembly 300b is positioned proximate to a portion of subsurface vasculature 307b within a body of a human 305b. The magnetic pole 320b comprises a layer of the high-permeability material disposed on a side of the magnetic assembly 300b opposite the human body 305b. The magnetic assembly 300b could be part of a wearable device and the wearable device could further include a mount configured to mount the wearable device to an external body surface of the body of the human 305b proximate to the portion of subsurface vasculature 307b. The magnetic elements 310b, 312b, 314b of the magnetic assembly 300b can be configured to exert a magnetic force on magnetic particles in the portion of subsurface vasculature 307b. The magnetic elements 310b, 312b, 314b being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic assembly and/or an environment of interest proximate to the magnetic assembly are anticipated. Further, the magnetic pole 320b could act to increase a property (e.g., a magnitude, a gradient magnitude) of the magnetic field produced by the magnetic assembly 300b in the portion of subsurface vasculature 307b and to decrease a property (e.g., a magnitude, a gradient magnitude) of the magnetic field produced by the magnetic assembly 300b in a region away from the body of the human 305b (i.e., to 'shield' the region below the magnetic assembly 300b from the magnetic field produced by the magnetic elements 310b, 312b, 314b).

Figure 3C:
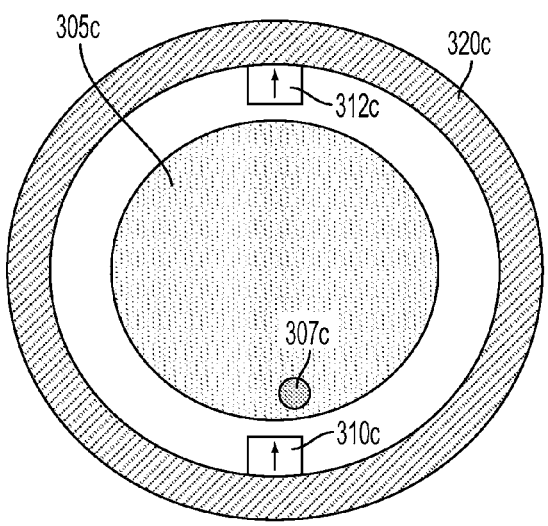
FIG. 3C is cross-sectional view of an example magnetic assembly, while positioned near a lumen of subsurface vasculature.

In some examples, the magnetic poles and/or magnetic elements of the magnetic assembly could wholly enclose an environment (e.g., a wrist or other body portion of a user). FIG. 3C illustrates a schematic diagram of an example magnetic assembly 300c comprising a plurality of magnetic elements (310c, 312c) having respective magnetic moments (arrows). The magnetic assembly 300c is positioned proximate to a portion of subsurface vasculature 307c within the body of a human 305c. The magnetic assembly 300c could be part of a wearable device and the wearable device could further include a mount configured to mount the wearable device to an external body surface of the body of the human 305c proximate to the portion of subsurface vasculature 307c. The magnetic assembly 300c wholly encloses a portion of the body of the human 307c with a magnetic pole 320c configured to transmit magnetic flux between the magnetic elements 310c, 312c to increase a property (e.g., a magnitude, a gradient magnitude) of the magnetic field produced by the magnetic assembly 300c in the portion of subsurface vasculature 307c and to decrease a property (e.g., a magnitude, a gradient magnitude) of the magnetic field produced by the magnetic assembly 300c outside of the enclosing magnetic pole 320c (i.e., to 'shield' the region outside of the enclosing magnetic pole 320c).

Figure 3D:
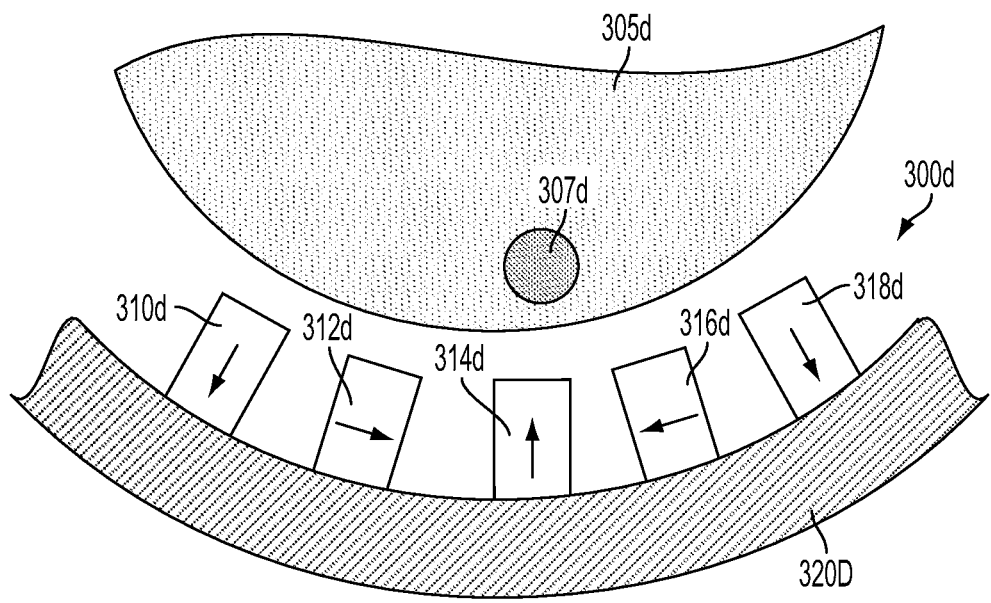
FIG. 3D is cross-sectional view of an example magnetic assembly, while positioned near a lumen of subsurface vasculature.

In some examples, the magnetic poles and/or magnetic elements of the magnetic assembly could partially enclose an environment (e.g., a wrist or other body portion of a user). FIG. 3D illustrates a schematic diagram of an example magnetic assembly 300d comprising a plurality of magnetic elements (310d, 312d, 314d, 316d, 318d) having respective magnetic moments (arrows). The magnetic assembly 300d is positioned proximate to a portion of subsurface vasculature 307d within a body of a human 305d. The magnetic assembly 300d could be part of a wearable device and the wearable device could further include a mount configured to mount the wearable device to an external body surface of the body of the human 305d proximate to the portion of subsurface vasculature 307d. The magnetic assembly 300d partially encloses a portion of the body of the human 307d with a magnetic pole 320d that is configured to increase a property (e.g., a magnitude, a gradient magnitude) of the magnetic field produced by the magnetic assembly 300d in the portion of subsurface vasculature 307d and to decrease a property (e.g., a magnitude, a gradient magnitude) of the magnetic field produced by the magnetic assembly 300d in a region away from the body of the human 305d (i.e., to 'shield' the region below the magnetic assembly 300d from the magnetic field produced by the magnetic elements 310d, 312d, 314d, 316d, 318d)

Figure 3E:
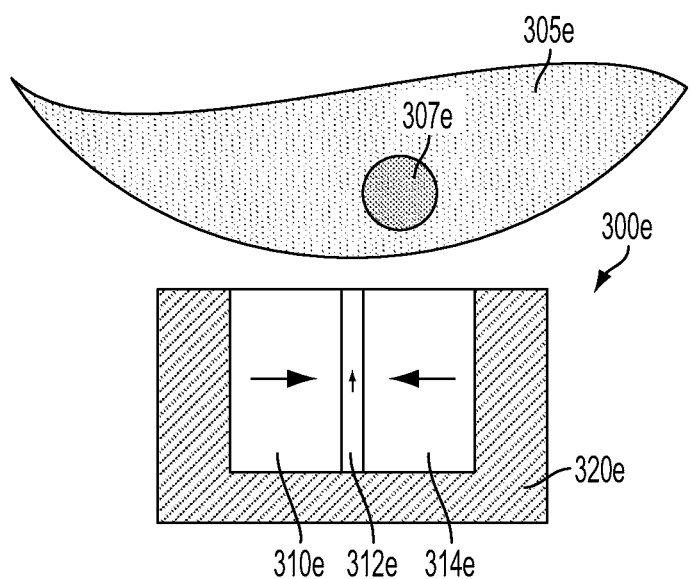
FIG. 3E is cross-sectional view of an example magnetic assembly, while positioned near a lumen of subsurface vasculature.

FIG. 3E illustrates a schematic diagram of an example magnetic assembly 300e comprising a plurality of magnetic elements 310e, 312e, 314e having respective magnetic moments (arrows) oriented such that the magnetic assembly forms a Halbach array, and such that a middle magnetic element 312e has a magnetic moment oriented toward a portion of subsurface vasculature 307e within a body of a human 305e. The magnetic assembly 300e additionally includes a magnetic pole 320e comprising a high-permeability material. The magnetic assembly 300e is positioned proximate to the portion of subsurface vasculature 307e within the body of the human 305e. The magnetic pole 320e comprises a layer of the high-permeability material disposed on at least three sides of the magnetic assembly 300e: opposite the human body 305e, opposite the left magnetic element 310e from the middle magnetic element 312e, and opposite the right magnetic element 314e from the middle magnetic element 312e. The magnetic assembly 300e could be part of a wearable device and the wearable device could further include a mount configured to mount the wearable device to an external body surface of the body of the human 305e proximate to the portion of subsurface vasculature 307e. The magnetic elements 310e, 312e, 314e of the magnetic assembly 300e can be configured to exert a magnetic force on magnetic particles in the portion of subsurface vasculature 307e. The magnetic elements 310e, 312e, 314e being arranged as a Halbach array comprises the orientation of the magnetic moment of an individual magnetic element being substantially perpendicular to (i.e., rotated approximated ninety degrees relative to) the magnetic moments of magnetic elements in the array adjacent to the individual magnetic element and substantially antiparallel to (i.e., rotated approximated 180 degrees relative to) magnetic elements in the array that are adjacent to the magnetic elements that are adjacent to the individual magnetic element. Other arrangements of the magnetic moments of magnetic elements of a magnetic array relative to the magnetic elements of the magnetic assembly and/or an environment of interest proximate to the magnetic assembly are anticipated. Further, the magnetic pole 320e could act to increase a property (e.g., a magnitude, a gradient magnitude) of the magnetic field produced by the magnetic assembly 300e in the portion of subsurface vasculature 307e and to decrease a property (e.g., a magnitude, a gradient magnitude) of the magnetic field produced by the magnetic assembly 300e in a region away from the body of the human 305e (i.e., to 'shield' the region below and/or to the sides of the magnetic assembly 300e from the magnetic field produced by the magnetic elements 310e, 312e, 314e).

In some embodiments, the magnetic assembly could have a narrowing geometry configured to concentrate a magnetic flux and/or to cause a magnetic field produced by the magnetic assembly to have a specified profile (i.e., a specified pattern of field magnitude, field direction, field gradient magnitude, field gradient direction) in one or more regions relative to the magnetic assembly. That is, an amount of flux and/or a magnitude of the magnetic field proximate to a narrow region of the narrowing geometry of the magnetic assembly (e.g., the 'top' peak of a truncated cone) could be greater than if the geometry did not narrow (e.g., the geometry was a cylinder, rather than a truncated cone). The narrowing geometry could include a magnetic pole and/or one or more permanent magnets. The narrowing geometry could be trapezoidal, conical, pyramidal, triangular, or some other narrowing geometry.

FIG. 4A illustrates a schematic diagram of an example magnetic assembly 400a comprising a magnetic flux source 410 and two magnetic poles 420a, 422a comprising a high-permeability material. The magnetic assembly 400a is positioned proximate to a portion of subsurface vasculature 407a within a body of a human 405a. The magnetic flux source 410a includes at least one permanent magnet, electromagnet or other magnetic flux-producing element. The magnetic flux source 410a can additionally include magnetic poles, air gaps, sensors, mechanically actuated elements (e.g., magnetic elements or other elements mounted to gears, gimbals, servos, or other actuators), or other components. In some examples, the magnetic flux source 410a could include a single magnetic element having a magnetic moment oriented toward the portion of subsurface vasculature 407a. In some examples, the magnetic flux source 410a could include a plurality of magnetic elements having respective magnetic moments oriented to form a Halbach array. A first magnetic pole 420a comprises a layer of the high-permeability material disposed on a side of the magnetic assembly 400a opposite the human body 405a. A second (i.e., focusing) magnetic pole 422a comprises the high-permeability material disposed on a side of the magnetic assembly 400a toward the human body 405a. The second magnetic pole 422a could have one of a variety of narrowing geometries such that a first cross-sectional area of the second magnetic pole 422a proximate to the magnetic flux source 410a is greater than a second cross-sectional area of the second magnetic pole 422a farther from the magnetic flux source 410a (i.e., proximate to the human body 405a).

The magnetic assembly 400a could be part of a wearable device and the wearable device could further include a mount configured to mount the wearable device to an external body surface of the body of the human 405a proximate to the portion of subsurface vasculature 407a. The magnetic flux source 410a and magnetic poles 420a, 422a of the magnetic assembly 400a can be configured to exert a magnetic force on magnetic particles in the portion of subsurface vasculature 407a. Further, the magnetic poles 420a, 422a could act to increase a property (e.g., a magnitude, a gradient magnitude) of the magnetic field produced by the magnetic assembly 400a in the portion of subsurface vasculature 407a (e.g., proximate to a narrow end of the second magnetic pole 422a) and to decrease a property (e.g., a magnitude, a gradient magnitude) of the magnetic field produced by the magnetic assembly 400a in a region away from the body of the human 405a (i.e., to 'shield' the region below the magnetic assembly 400a from the magnetic field produced by the magnetic flux source 410a).

The second magnetic pole 422a could have a narrowing geometry chosen from a variety of narrowing geometries. The second magnetic pole 422a could be conical, pyramidal (e.g., a triangular pyramid, a square pyramid, a pyramid having some arbitrary polygonal base), a triangular prism, a partial ellipsoidal prism, a partial ellipsoid, or have some other narrowing or tapering geometry. The second magnetic pole 422a could have a truncated narrowing geometry (e.g., a truncated cone, a truncated pyramid, a trapezoidal prism). The second magnetic pole 422a could have a narrowing cross-sectional shape in a plane substantially perpendicular an external body surface of the human 405a proximate to which the magnetic assembly 400a is positioned. For example, the second magnetic pole 422a could have a triangular cross-section, a trapezoidal cross-section, a partial elliptical cross-section, or some other narrowing shape cross-section.

Elements (e.g., 410a, 420a, 422a) of the magnetic assembly 400a could have specified properties (e.g., sizes, thicknesses, widths, lengths, compositions, shapes) chosen so as to optimize certain properties of the magnetic assembly (e.g., a magnetic field magnitude, a magnetic field gradient magnitude) given one or more constraints on the magnetic assembly (e.g., a maximum volume, a maximum mass, a specified permanent magnet geometry). In some examples, the geometry of the second (focusing) magnetic pole 422a could be specified to maximize the magnetic field magnitude and the magnetic field gradient magnitude proximate to the second magnetic pole 422a for a given small size of magnetic flux source 410a (e.g., a small permanent (e.g., Nd52) magnet). For example, the second magnetic pole 422a could have a length of 5 millimeters, a width of 5 millimeters, a thickness of 2 millimeters, and could have a truncated pyramid geometry wherein the flat top of the truncated pyramid had a width of 1 millimeter. In some examples, the second magnetic pole 422a could have a size and/or geometry relative to other elements of the magnetic assembly 400a such that the second magnetic pole 422a is magnetically saturated. Other geometries and dimensions of elements of a magnetic assembly are anticipated.

Additionally or alternatively, one or more permanent magnets of a magnetic assembly could have a narrowing geometry. FIG. 4B illustrates a schematic diagram of an example magnetic assembly 400b comprising a plurality of permanent magnets 410b, 412b, 414b having respective magnetic moments (arrows) that have, together, a narrowing geometry and whose magnetic moments are oriented such that the magnetic assembly forms a Halbach array. The magnetic assembly 400b additionally includes a magnetic pole 420a comprising a high-permeability material. The magnetic assembly 400b is positioned proximate to a portion of subsurface vasculature 407b within a body of a human 405b. The magnetic pole 420b comprises a layer of the high-permeability material disposed on a side of the magnetic assembly 400b opposite the human body 405b. The permanent magnets 410b, 412b, 414b could have one of a variety of narrowing geometries such that a cross-sectional shape of the permanent magnets 410b, 412b, 414b in a plane substantially perpendicular to an external body surface of the body of the human 405b proximate to the portion of subsurface vasculature 407b was narrower proximate to the external body surface.

The magnetic assembly 400b could be part of a wearable device and the wearable device could further include a mount configured to mount the wearable device to an external body surface of the body of the human 405b proximate to the portion of subsurface vasculature 407b. The permanent magnets 410b, 412b, 414b of the magnetic assembly 400b can be configured to exert a magnetic force on magnetic particles in the portion of subsurface vasculature 407b. The permanent magnets 410b, 412b, 414b being arranged as a Halbach array comprises the orientation of the magnetic moment of an individual permanent magnet being substantially perpendicular to (i.e., rotated approximated ninety degrees relative to) the magnetic moments of permanent magnets in the array adjacent to the individual permanent magnet and substantially antiparallel to (i.e., rotated approximated 180 degrees relative to) permanent magnets in the array that are adjacent to the permanent magnets that are adjacent to the individual permanent magnet. Other arrangements of the magnetic moments of permanent magnets of a magnetic array relative to the permanent magnets of the magnetic assembly and/or an environment of interest proximate to the magnetic assembly are anticipated. Further, the magnetic pole 420b could act to increase a property (e.g., a magnitude, a gradient magnitude) of the magnetic field produced by the magnetic assembly 400b in the portion of subsurface vasculature 407b and to decrease a property (e.g., a magnitude, a gradient magnitude) of the magnetic field produced by the magnetic assembly 400b in a region away from the body of the human 405b (i.e., to 'shield' the region below the magnetic assembly 400b from the magnetic field produced by the permanent magnets 410b, 412b, 414b).

The permanent magnets 410b, 412b, 414b could have a narrowing geometry chosen from a variety of narrowing geometries. The permanent magnets 410b, 412b, 414b could be conical, pyramidal (e.g., a triangular pyramid, a square pyramid, a pyramid having some arbitrary polygonal base), a triangular prism, a partial ellipsoidal prism, a partial ellipsoid, or have some other narrowing or tapering geometry. The permanent magnets 410b, 412b, 414b could have a truncated narrowing geometry (e.g., a truncated cone, a truncated pyramid, a trapezoidal prism). The permanent magnets 410b, 412b, 414b could have a narrowing cross-sectional shape in a plane substantially perpendicular an external body surface of the human 405b proximate to which the magnetic assembly 400b is positioned. For example, the permanent magnets 410b, 412b, 414b could have a triangular cross-section, a trapezoidal cross-section, a partial elliptical cross-section, or some other narrowing shape cross-section.

FIG. 5 illustrates a schematic diagram of an example magnetic assembly 500 comprising a magnetic pole 520 and a plurality of magnetic elements 510, 512, 514, 516 having respective magnetic moments (arrows). The magnetic assembly 500 is positioned proximate to a portion of subsurface vasculature 507 within a body of a human 505. The magnetic assembly 500 could be part of a wearable device and the wearable device could further include a mount configured to mount the wearable device to an external body surface of the body of the human 505 proximate to the portion of subsurface vasculature 507. The magnetic assembly 500 partially encloses a portion of the body of the human 507; that is, the magnetic elements 510, 512, 514, 516 are disposed on a concave surface of the magnetic device 500 and the concave surface is configured to partially enclose a convex surface (i.e., the external body surface) of the human 507. The magnetic pole 520 is configured to increase a property (e.g., a magnitude, a gradient magnitude) of the magnetic field produced by the magnetic assembly 500 in the portion of subsurface vasculature 507 and to decrease a property (e.g., a magnitude, a gradient magnitude) of the magnetic field produced by the magnetic assembly 500 in a region away from the body of the human 505 (i.e., to 'shield' the region below the magnetic assembly 500 from the magnetic field produced by the magnetic elements 510, 512, 514, 516). First 510 and third 514 magnetic elements have magnetic moments pointing into respective proximate regions of the external body surface of the human 505 and third 512 and fourth 516 magnetic elements have magnetic moments pointing away from respective proximate regions of the external body surface of the human 505.

Magnetic assemblies, devices containing magnetic assemblies, magnetic particles, and other aspects and embodiments described herein (e.g., 200a, 200b, 200c, 200d, 300a, 300b, 300c, 300d, 300e, 400a, 400b, 500) could be configured and/or operated to provide a variety of applications. In some examples, magnetic particles could be configured to bind to an analyte of interest, and a magnetic assembly could be configured to collect or otherwise manipulate the magnetic particles to enable the detection, extraction, modification, or other manipulation of the analyte. For example, a detector could be disposed proximate to a magnetic assembly that is configured to collect the magnetic particles, and the detector could detect one or more properties of the analyte bound to the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the collected magnetic particles sufficient to alter one or more properties of the analyte (e.g., to destroy, denature, heat, change a conformation state of, other otherwise modify the analyte). In some examples, collection of an analyte bound to magnetic particles by a magnetic assembly could enable the extraction of the analyte and magnetic particles (e.g., using a hypodermic needle).

In some applications, manipulation of magnetic particles could enable detection and/or modification of an analyte. For example, the reaction (e.g., a differential and/or absolute motion) of a magnetic particle to a magnetic field generated by a magnetic assembly (e.g., 200a, 200b, 200c, 200d, 300a, 300b, 300c, 300d, 300e, 400a, 400b, 500) could be detected, and one or more properties of the reaction could be used to determine one or more properties of the magnetic particle. For example, the degree change in velocity of a magnetic particle, when exposed to the magnetic field of the magnetic assembly, could be related to whether the magnetic particle was bound to an analyte. In some examples, the magnetic particles could be configured to couple an oscillating electromagnetic field into an increase in heat proximate to the magnetic particle, and this increase in heat could be used to detect one or more properties of the magnetic particle and/or to modify the environment proximate to the particle (e.g., to denature an analyte bound to the magnetic particle). Other configurations, operations, and applications of the embodiments described herein are anticipated.

Figure 6:
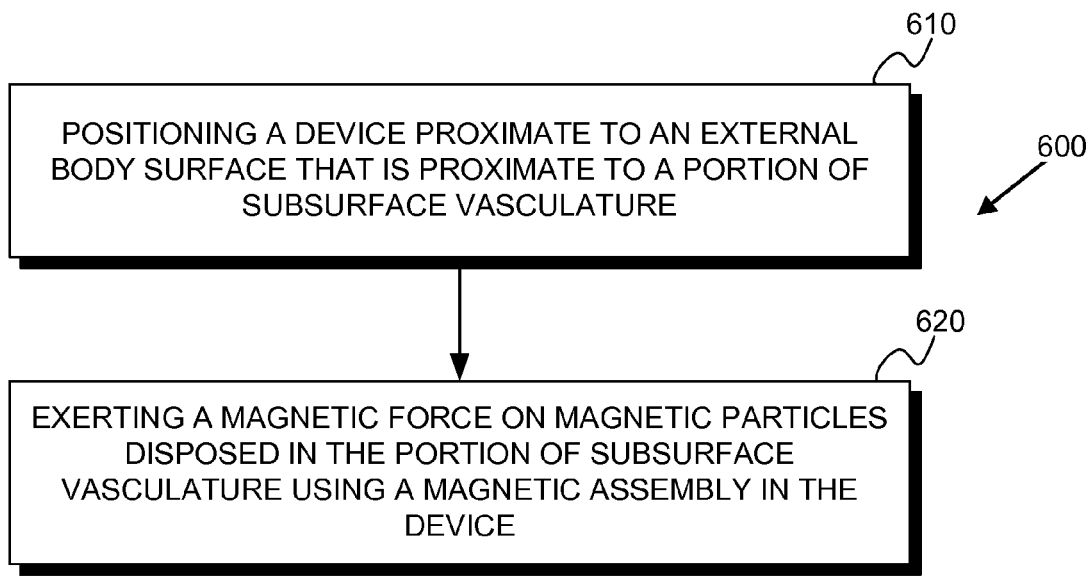
FIG. 6 is a flowchart of an example method

IV. Illustrative Methods for Using a Magnetic Assembly to Exert Forces on Magnetic Particles FIG. 6 is a flowchart of an example method 600 for exerting a magnetic force on magnetic particles using a device. The device includes a magnetic assembly comprising a plurality of magnetic elements such that, when the device is positioned proximate to an external body surface that is proximate to a portion of subsurface vasculature, at least a first magnetic element of the magnetic assembly provides a magnetic moment oriented toward the portion of subsurface vasculature and a second magnetic element of the magnetic assembly provides a magnetic moment oriented in a different direction. The method 600 includes positioning the device onto the external surface proximate to the portion of subsurface vasculature 610. This could include operating a mount included in the device that is configured to enclose a portion of the body of a user (e.g., a wrist, an ankle, a chest) to secure the magnetic assembly at a specified location relative to the portion of subsurface vasculature. In some examples, this could include positioning the magnetic device relative to a visible or other landmark on or beneath the external body surface (e.g., a tattoo, a visible artery or vein, bony protuberance, a joint, a birth mark). In some examples, this could include manipulating and/or changing the location of the device relative to some indication from the device, e.g., and indication from the device that the magnetic assembly was located proximate to the portion of subsurface vasculature.

The method 600 additionally includes exerting a magnetic force on magnetic particles disposed in the portion of subsurface vasculature using the magnetic assembly disposed in the device 620. This could include exerting an attractive force on the magnetic particles sufficient to collect the magnetic particles in the portion of subsurface vasculature. This could include exerting a magnetic force having a direction substantially parallel to a direction of blood flow in the portion of subsurface vasculature. Other examples of exerting a magnetic force on magnetic particles using the device and applications thereof are anticipated. Further, exerting a magnetic force 620 could include applying a voltage and/or current to any magnetic elements of the plurality of magnetic elements of the device that are electromagnets.

The method 600 could include additional steps or elements. For example, the method 600 could include introducing the magnetic particles into the portion of subsurface vasculature (e.g., injecting, ingesting, transdermally transferring, or otherwise introducing the engineered particles into a lumen of vasculature of a human). In some examples, the magnetic particles could be configured to bind to an analyte and to enable detection of one or more properties of, modification of one or more properties of, and/or some other interaction with the analyte.

In some examples, the method 600 could include detecting one or more properties of an analyte to which the magnetic particles are configured to bind. This could include operating a detector of the device to detect the one or more properties of the bound analyte. In some examples, this could include exerting an attractive magnetic force on the magnetic particles such that the magnetic particles and instances of the analyte bound thereto are caused to collect in a portion of subsurface vasculature proximate to the magnetic assembly and/or the detector of the device. In some examples, this could include exerting a first magnetic force on first magnetic particles that are bound to the analyte and exerting a second magnetic force on second magnetic particles that are not bound to the analyte such that the first and second magnetic particles are separated such that a detector of the device substantially only detects one or more properties of the first set of magnetic particles. Other methods of detecting one or more properties of an analyte using a magnetic assembly disposed in a device positioned proximate to a portion of subsurface vasculature are anticipated.

In some examples, the method 600 could include altering a clearance rate (i.e., a rate at which a substance is removed from an environment) of an analyte out of the portion of subsurface vasculature and/or out of some other region of a user's body (e.g., out of the blood of the user) using the magnetic assembly of the device. This could include exerting an attractive magnetic force on magnetic particles disposed in the portion of subsurface vasculature that are configured to bind to the analyte. The attractive magnetic force could be sufficient to collect the magnetic particles and instances of the analyte bound thereto in the portion of subsurface vasculature proximate to the device. Collection of the magnetic particles configured to bind to the analyte act to alter (e.g., to reduce) a rate of clearance of the analyte from the body of the user (e.g., by collecting the analyte in the portion of subsurface vasculature such that less of the analyte is available to be cleared from the body of the user by e.g., kidneys of the user). Other methods of using the device and/or magnetic particles to affect a clearance rate, a reaction rate, a rate of decomposition and/or deactivation, an effectiveness, a chemical activity, or some other property or properties of an analyte are anticipated.

V. Example Wearable Devices

Figure 7:
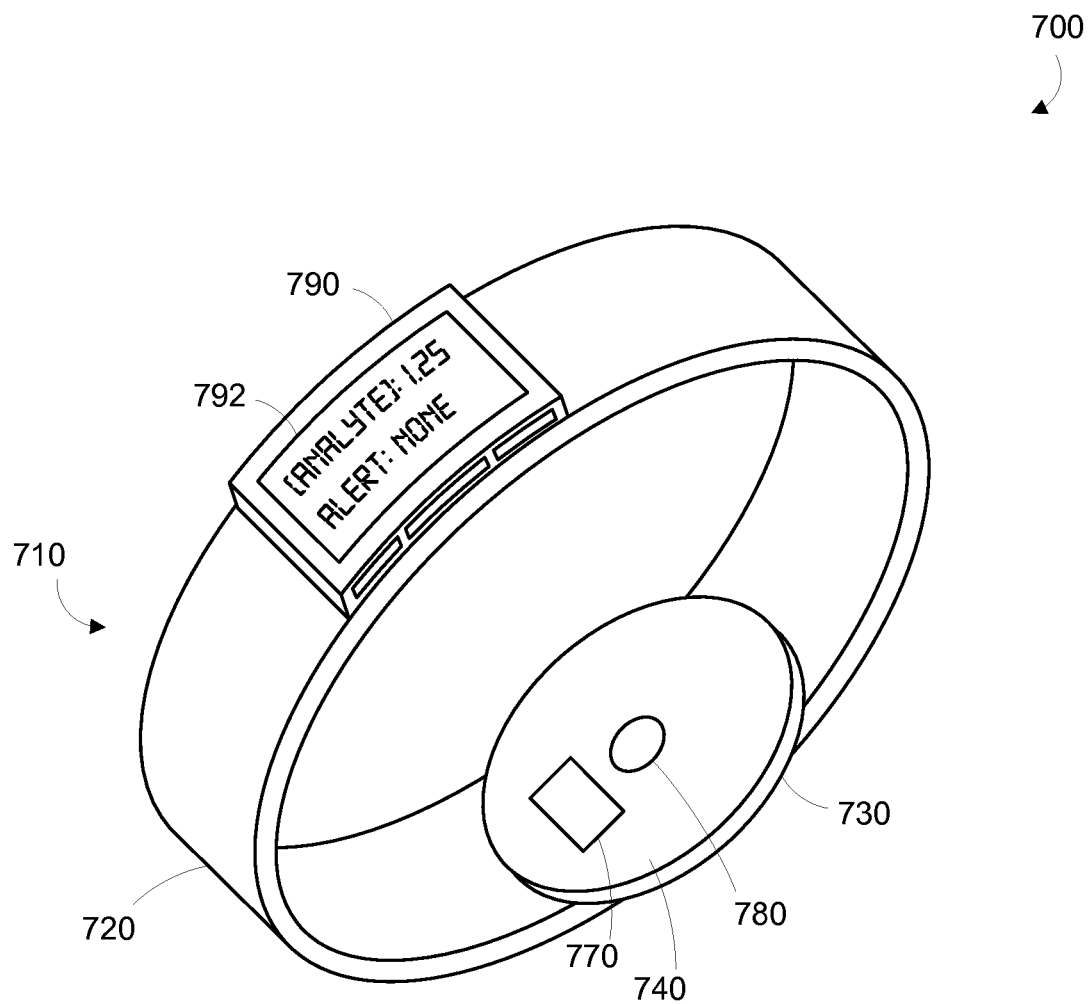
FIG. 7 is a perspective view of an example wearable device.

A wearable device 700 can measure a plurality of physiological parameters of a person wearing the device, among other functions. Some or all of the functions of the wearable device 700 are enabled by collection, separation, or some other manipulation of magnetic particles in blood of the wearer of the device. Such manipulations can be effected by the exertion of magnetic forces on the magnetic particles by a magnetic assembly (e.g., 170a, 170b, 170c, 170d, 200a, 200b, 200c, 200d, 300a, 300b, 300c, 300d, 300e, 400a, 400b, 500) disposed on or in the wearable device 700. The term "wearable device," as used in this disclosure, refers to any device that is capable of being worn at, on or in proximity to a body surface, such as a wrist, ankle, waist, chest, or other body part. In order to manipulate magnetic particles and/or take in vivo measurements in a non-invasive manner from outside of the body, the wearable device may be positioned on a portion of the body where subsurface vasculature containing magnetic particles is easily affectable (e.g., by exertion of magnetic forces) and observable, depending on the type of modification and detection systems used. The device may be placed in close proximity to the skin or tissue, but need not be touching or in intimate contact therewith. A mount 710, such as a belt, wristband, ankle band, etc. can be provided to mount the device at, on or in proximity to the body surface. The mount 710 may prevent the wearable device 700 from moving relative to the body to ensure effective manipulation of magnetic particles and/or detection of one or more physiological properties of the wearer. In one example, shown in FIG. 7, the mount 710, may take the form of a strap or band 720 that can be worn around a part of the body. Further, the mount 710 may include an adhesive material for adhering the wearable device 700 to the body of a wearer.

A manipulation platform 730 is disposed on the mount 710 such that it can be positioned on the body where subsurface vasculature is easily affected. An inner face 740 of the manipulation platform 730 is intended to be mounted facing to the body surface. The manipulation platform 730 may house a magnetic assembly 780. In such embodiments, the magnetic assembly 780 could be configured to separate collect, separate, or otherwise manipulate particles in a portion of subsurface vasculature by exerting magnetic forces on the magnetic particles. The magnetic assembly 780 could include electromagnets, permanent magnets, magnetic shims, or other magnetic material configured in a variety of ways (e.g., configured similarly to magnetic assemblies 200a, 200b, 200c, 200d, 300a, 300b, 300c, 300d, 300e, 400a, 400b, 500).

In some examples, the wearable device 700 further includes at least one detector 770 for detecting at least one physiological parameter, which could include any parameters that may relate to the health of the person wearing the wearable device. For example, the detector 770 could be configured to measure blood pressure, pulse rate, respiration rate, skin temperature, etc. At least one of the detectors 770 could be configured to non-invasively measure one or more properties of magnetic particles in blood and/or analytes bound thereto circulating in subsurface vasculature proximate to the wearable device. In a non-exhaustive list, detector 770 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., RF, magnetic resonance) sensor. Operation of the detector 770 could be related to and/or contingent on collection, separation, or some other manipulation of magnetic particles by the magnetic assembly 780.

The wearable device 700 may also include a user interface 790 via which the wearer of the device may receive one or more recommendations or alerts generated from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 790 may include a display 792 where a visual indication of the alert or recommendation may be displayed. The display 792 may further be configured to provide an indication the battery status of the device or the status of the modification system or an indication of any measured physiological parameters, for instance, the concentrations of certain blood analytes being measured.

Figure 8A:
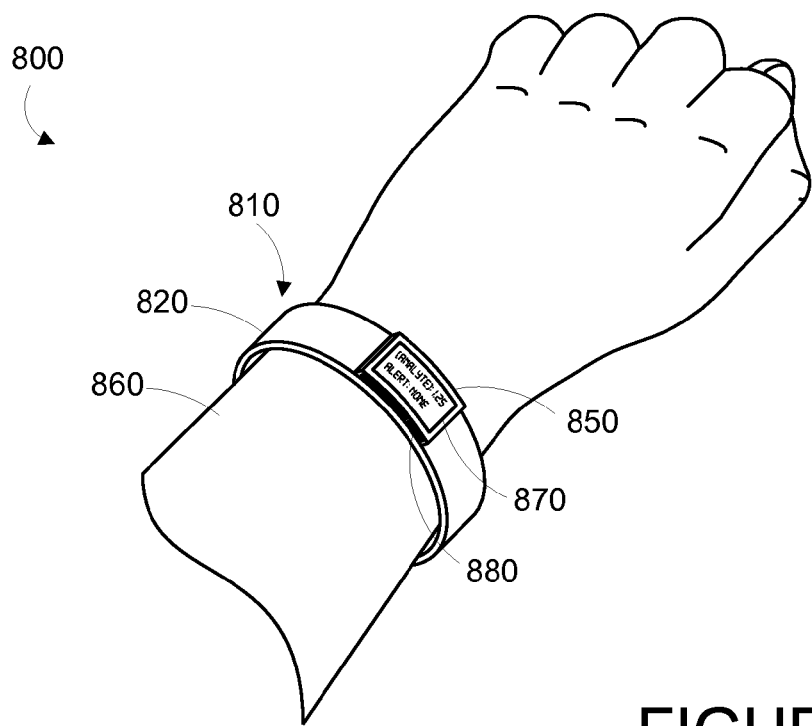
FIG. 8A is a perspective top view of an example wrist-mounted device, when mounted on a wearer's wrist.
Figure 8B:
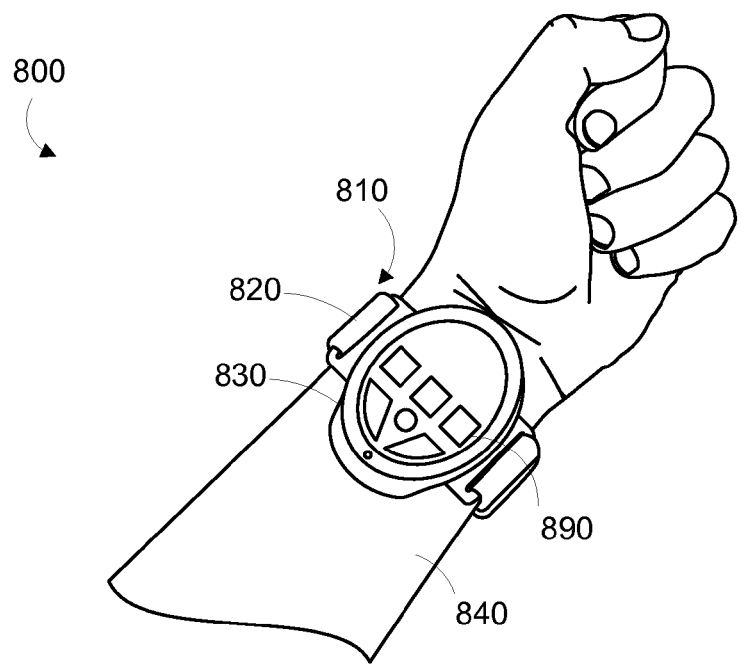
FIG. 8B is a perspective bottom view of an example wrist-mounted device shown in FIG. 8A, when mounted on a wearer's wrist.

In one example, the wearable device is provided as a wrist-mounted device, as shown in FIGS. 8A and 8B. The wrist-mounted device may be mounted to the wrist of a living subject with a wristband or cuff, similar to a watch or bracelet. As shown in FIGS. 8A and 8B, the wrist mounted device 800 may include a mount 810 in the form of a wristband 820, a manipulation platform 830 positioned on the anterior side 840 of the wearer's wrist, and a user interface 850 positioned on the posterior side 860 of the wearer's wrist. The wearer of the device may receive, via the user interface 850, one or more recommendations or alerts generated either from a remote server or other remote computing device, or alerts based on physiological properties of a wearer detected by the wrist-mounted device 800. Such a configuration may be perceived as natural for the wearer of the device in that it is common for the posterior side 860 of the wrist to be observed, such as the act of checking a wrist-watch. Accordingly, the wearer may easily view a display 870 on the user interface. Further, the manipulation platform 830 may be located on the anterior side 840 of the wearer's wrist where the subsurface vasculature may be readily affectable. However, other configurations are contemplated.

The display 870 may be configured to display a visual indication of the alert or recommendation and/or an indication of the status of the wearable device and an indication of measured physiological parameters, for instance, the concentrations of certain target blood analytes bound to collected, separated, or otherwise magnetically manipulated magnetic particles in the blood. Further, the user interface 850 may include one or more buttons 880 for accepting inputs from the wearer. For example, the buttons 880 may be configured to change the text or other information visible on the display 870. As shown in FIG. 8B, manipulation platform 830 may also include one or more buttons 890 for accepting inputs from the wearer. The buttons 890 may be configured to accept inputs for controlling aspects of the wrist-mounted device 800, such as inputs indicating the

CONCLUSION

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

While various aspects and embodiments herein are described in connection with exerting forces on magnetic particles disposed in a portion of subsurface vasculature, other applications and environments are possible. Aspects and embodiments herein could be applied to exert forces on magnetic particles in in vivo or in vitro human or animal tissues, a fluid in a scientific, medical, or industrial testing process, or some other environment. Magnetic forces could be exerted on magnetic particles disposed in a natural environment, e.g., a lake, river, stream, marsh, or other natural locale. Magnetic forces could be exerted on magnetic particles disposed in a fluid environment of an industrial process or other artificial environment, e.g., a water treatment process, a food preparation process, a pharmaceutical synthesis process, a chemical synthesis process, a brewing and/or distilling process, or other artificial locale. Magnetic forces could be exerted on magnetic particles disposed in an environment that includes a flowing fluid (e.g., fluid flowing in a blood vessel, a pipe, a culvert) and/or a static fluid. Other environments and applications of aspects and embodiments described herein are anticipated.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A device comprising:
    a magnetic assembly comprising a plurality of magnetic elements and a layer of high-permeability magnetic material, wherein the magnetic assembly has a first side and a second side opposite the first side, wherein the layer of high-permeability magnetic material is disposed on the second side,
    wherein the plurality of magnetic elements includes at least a first magnetic element to provide a first magnetic moment and a second magnetic element to provide a second magnetic moment, wherein the first and second magnetic moments have different orientations, such that when the first side of the magnetic assembly is positioned proximate to an external body surface (i) the first magnetic moment is oriented toward a portion of subsurface vasculature proximate to the external body surface and the second magnetic moment has a different orientation than the first magnetic moment and (ii) the magnetic assembly exerts a magnetic force on magnetic particles adapted to be placed in the portion of subsurface vasculature, wherein the magnetic particles are configured to bind to an analyte; and
    a detector, wherein the detector is configured to detect one or more properties of the analyte bound to the magnetic particles.

2. The device of claim 1, wherein the first magnetic element is either a permanent magnet or an electromagnet and the second magnetic element is either a permanent magnet or an electromagnet.

3. The device of claim 2, wherein the magnetic force is an attractive magnetic force, and wherein the attractive magnetic force is sufficient to collect the magnetic particles in the subsurface vasculature proximate to the magnetic assembly.

4. The device of claim 1, wherein the magnetic particles include first magnetic particles and second magnetic particles, wherein the magnetic assembly exerts a magnetic force on magnetic particles that are disposed in the portion of subsurface vasculature including a first magnetic force on the first magnetic particles and a second magnetic force on the second magnetic particles, and wherein the first magnetic force and the second magnetic force are sufficiently different to cause separation of the first magnetic particles and the second magnetic particles.

5. The device of claim 1, wherein the plurality of magnetic elements comprises at least three magnetic elements, wherein the first magnetic element is adjacent to the second magnetic element, wherein the second magnetic element is adjacent to a third magnetic element of the at least three magnetic elements, wherein the third magnetic element has a third magnetic moment, wherein the second magnetic moment is perpendicular to the first magnetic moment, wherein the third magnetic moment is perpendicular to the second magnetic moment, wherein the third magnetic moment is antiparallel to the first magnetic moment, and wherein at least one of the at least three magnetic elements has a magnetic moment that is oriented perpendicularly to the external body surface when positioned proximate the external body surface.

6. The device of claim 5, wherein the at least three magnetic elements are permanent magnets, and wherein the at least three magnetic elements have a cross-sectional shape, wherein the cross-sectional shape is narrower proximate to the external body surface.

7. The device of claim 1, wherein the magnetic assembly further comprises a focusing pole comprising a high-permeability magnetic material, wherein the focusing pole is disposed on the first side of the magnetic assembly, wherein the focusing pole has a first cross-sectional area proximate to a first side of the first magnetic element, wherein the focusing pole has a second cross-sectional area farther from the first side of the first magnetic element, and wherein the second cross-sectional area is less than the first cross-sectional area.

8. The device of claim 7, wherein the focusing pole has a cross-sectional shape, wherein the cross-sectional shape is trapezoidal.

9. The device of claim 1, wherein the magnetic assembly has a concave surface, the external body surface has a convex surface, and the concave surface is configured to at least partially enclose the convex surface.

10. The device of claim 9, wherein at least two of the plurality of magnetic elements are disposed on the concave surface.

11. The device of claim 10, wherein the plurality of magnetic elements includes four magnetic elements disposed on the concave surface, wherein each of the four magnetic elements has a respective magnetic moment that is perpendicular to a respective local external body surface, wherein a first magnetic element of the four magnetic elements has a magnetic moment pointing into the respective local external body surface, wherein a second magnetic element of the four magnetic elements has a magnetic moment pointing away from the respective local external body surface, wherein the second magnetic element is proximate to the first magnetic element, wherein a third magnetic element of the four magnetic elements has a magnetic moment pointing into the respective local external body surface, wherein the third magnetic element is proximate to the second magnetic element, wherein the third magnetic element is disposed opposite the first magnetic element relative to the second magnetic element, wherein the magnetic moment of the third magnetic element is antiparallel to the magnetic moment of the second magnetic element, wherein a fourth magnetic element of the four magnetic elements has a magnetic moment pointing away from the respective local external body surface, wherein the fourth magnetic element is proximate to the third magnetic element, wherein the fourth magnetic element is disposed opposite the second magnetic element relative to the third magnetic element.

12. The device of claim 1, wherein the layer of high-permeability magnetic material comprises mu-metal, iron, steel, metglas, Permalloy, or ferrite.

* * * * *